United States Patent
Borschneck et al.

[11] Patent Number: 5,891,066
[45] Date of Patent: Apr. 6, 1999

[54] COMBINED BIOHAZARD BARRIER AND SPLINTING DEVICE

[75] Inventors: Anthony G. Borschneck, 770 Flower Ash La., Redding, Calif. 96003; Ronald A. Yapp, Phoenix, Ariz.

[73] Assignee: Anthony G. Borschneck, Redding, Calif.

[21] Appl. No.: 46,029

[22] Filed: Mar. 23, 1998

[51] Int. Cl.[6] ............................................. A61F 5/00
[52] U.S. Cl. .................................................... 602/5
[58] Field of Search ...................... 602/5, 23, 24, 602/32, 36, 38; 128/870, 882

[56] References Cited

U.S. PATENT DOCUMENTS

| | | | |
|---|---|---|---|
| 2,785,672 | 3/1957 | Napoli | 602/5 |
| 3,738,358 | 6/1973 | Hallett | 602/5 |
| 3,750,659 | 8/1973 | Loomans | 602/23 |
| 3,896,799 | 7/1975 | Seeley | 602/5 |
| 4,328,794 | 5/1982 | Holmes | 602/5 |
| 4,608,971 | 9/1986 | Borschneck | 602/23 |
| 5,074,289 | 12/1991 | Leibinsohn | 602/23 |
| 5,146,932 | 9/1992 | McCabe | 602/23 X |
| 5,162,039 | 11/1992 | Dahners | 602/23 |
| 5,669,908 | 9/1997 | Gracilla | 602/23 X |
| 5,718,669 | 2/1998 | Marble | 602/5 |

*Primary Examiner*—Linda C. M. Dvorak
*Attorney, Agent, or Firm*—Lothrop & West

[57] ABSTRACT

A bag-like container of flexible plastic material snugly confines the ischial padding and body of an emergency traction splint for an injured leg while allowing access to the traction-inducing components thereof. Additional biohazard shielding is afforded by an integral cover of flexible, impervious material sufficiently rigid to provide a protective enclosure for patient transport. The container and the cover as well as the attendant malleolar harness are disposable. A barrier against cross-contamination from biohazards present in human body fluids is provided.

11 Claims, 6 Drawing Sheets

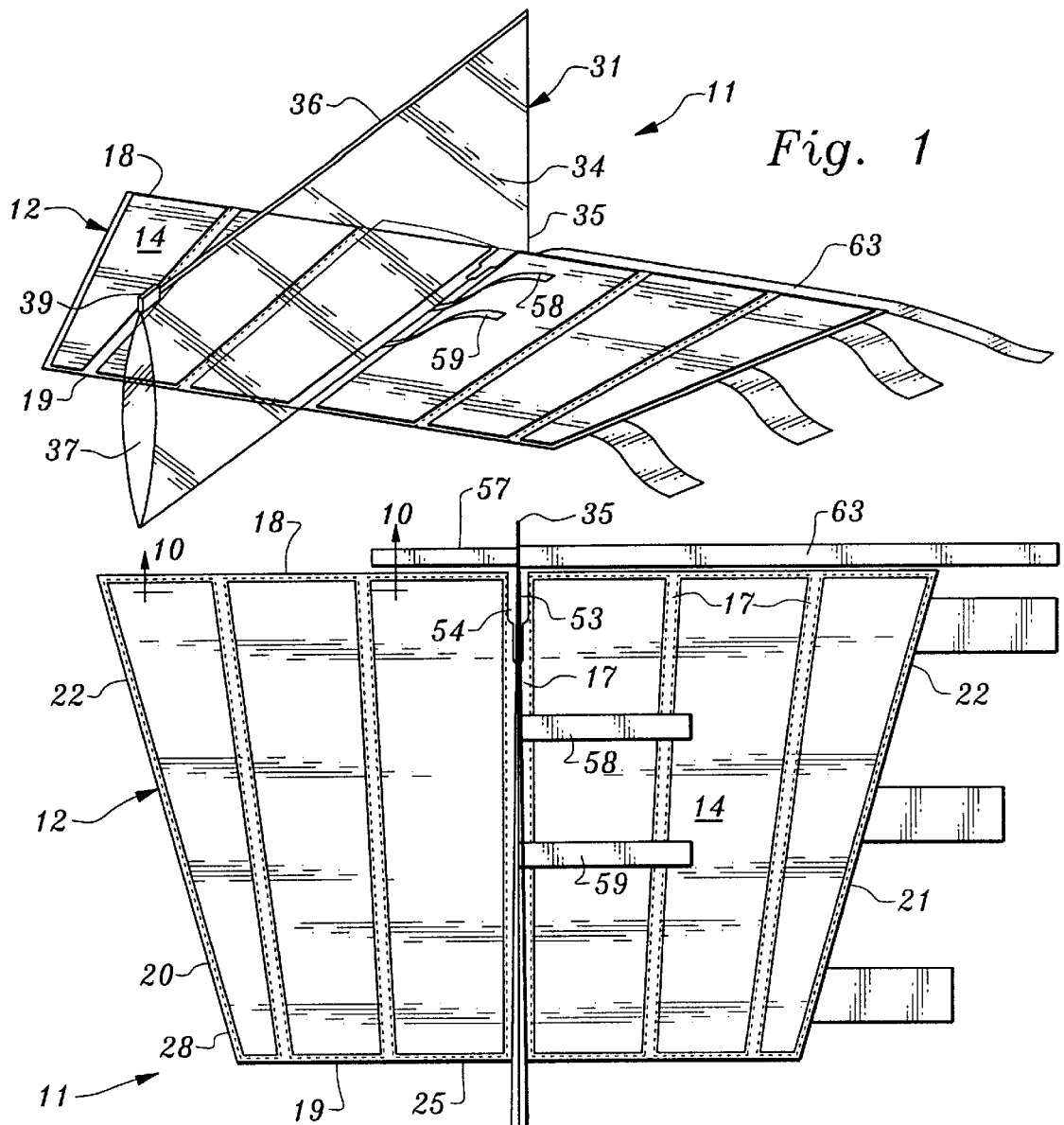
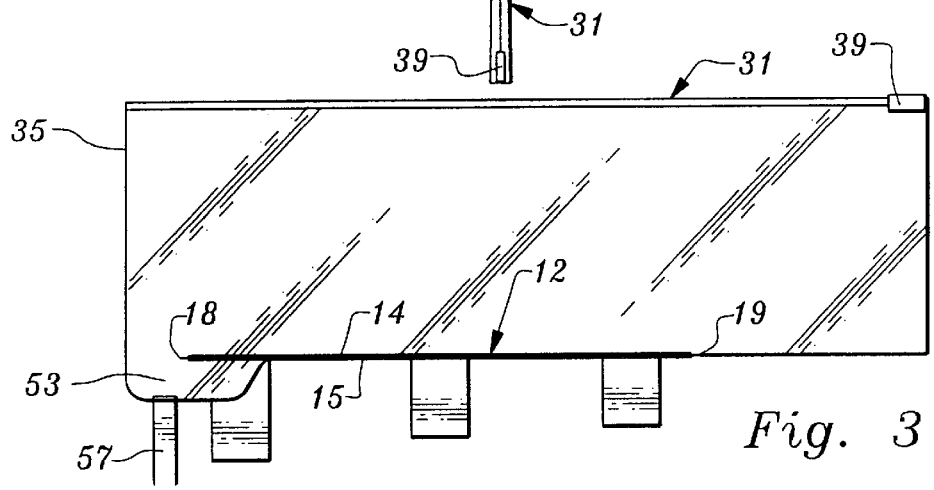
Fig. 1
Fig. 2
Fig. 3

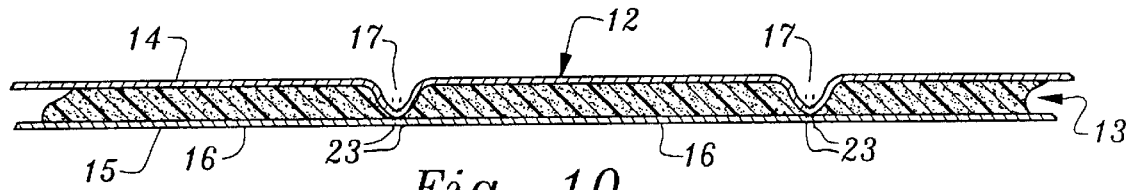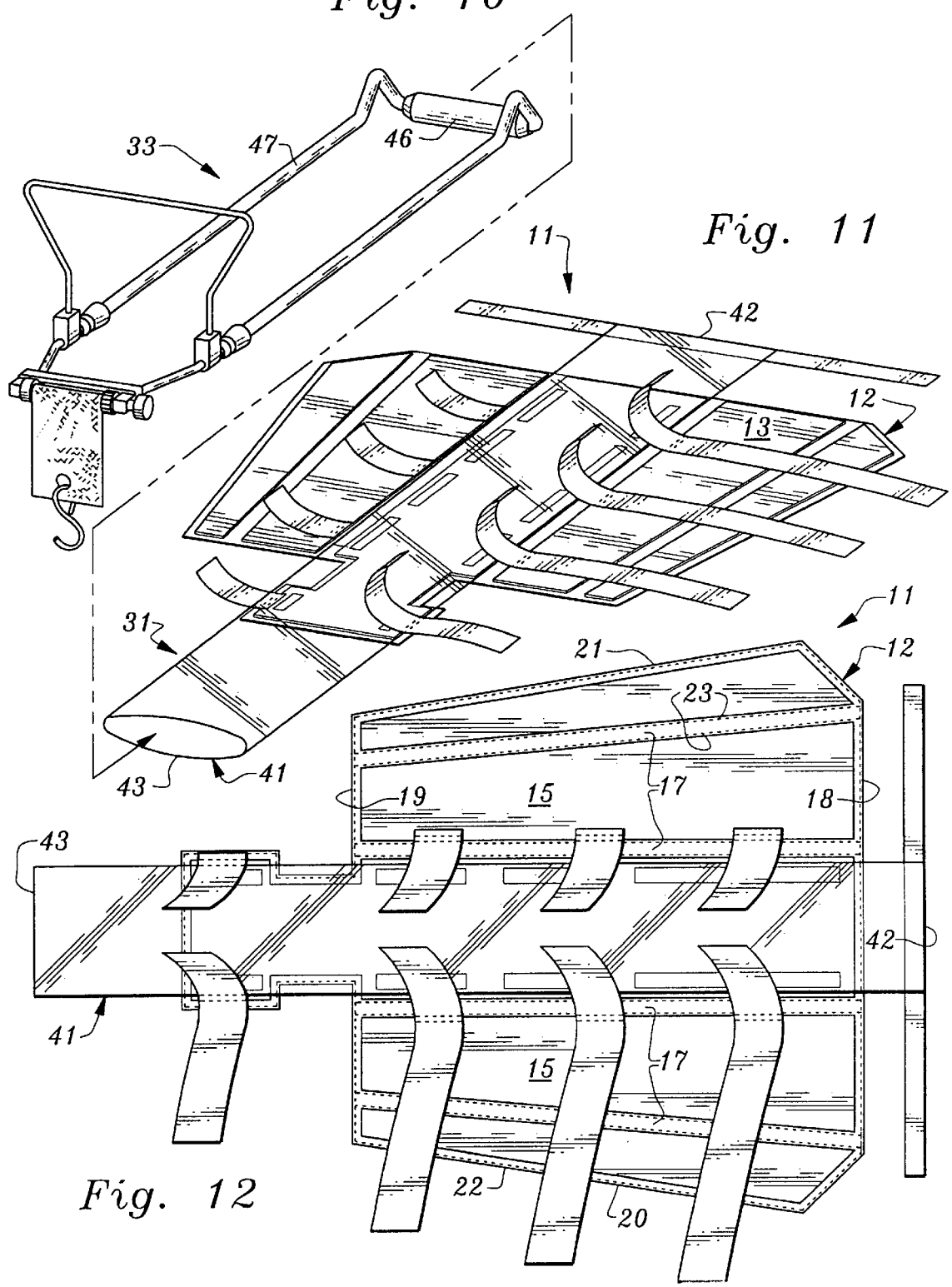

//5,891,066//

COMBINED BIOHAZARD BARRIER AND SPLINTING DEVICE

BACKGROUND OF THE INVENTION

The invention relates generally to emergency traction splints for a human patient whose leg or legs have been fractured or otherwise seriously injured, in an automobile accident, for example. More particularly, the invention relates to emergency leg splints which also afford a shield, or barrier, against cross-contamination between successive patients from biohazards present in human blood, urine, feces and other body fluids.

Emergency traction splints and components thereof are well known, both in the patent literature and in the marketplace. Exemplary are the various models of SAGER® Emergency Traction Splints. Several of these models have been developed by Anthony G. Borschneck, M.d., one of the applicants herein and patentee under U.S. Pat. Nos. 4,350,153; 4,463,750; and, 4,608,971 inter alia.

Another form of emergency leg splint, variously known as a crossbar ischial pad traction splint, or Ischial Pad splint, or Half Ring Splint, is disclosed in expired U.S. Pat. No. 3,477,428.

SUMMARY OF THE INVENTION

Both types of the above-identified traction splints are illustrated in the present application, along with covers, or enclosures, developed for particular use with these two types of splints. Where necessary, individual components of both splints, per se, are described. For details of construction and operation, however, reference may be had to the above-recited patents.

The present invention is a combination of presently known emergency traction devices, together with a biohazard barrier in the form of an impervious flexible bag enclosing the traction devices and a sheet of impervious, flexible, cushioned material capable of being folded into an enclosure, or cover, enveloping both the traction device and the bag, as well as the injured leg, in snug relation. The snug relation is maintained by elongated flaps, strips and bands provided with adhesive protected by peel-off covers until ready for use, or by VELCRO®, or the like. An ankle harness accompanies each embodiment and the bag along with the enclosure and the ankle harness are disposable.

The combination affords the following advantages over currently available emergency traction splints:

a. Protects against cross-contamination;

b. Superior splinting capability when applied to any known splinting devices;

c. Cover may be used as a good splint even without a traction splint;

d. Universal fit for human beings of any age and size;

e. Readily applied; and, f. Disposable.

SHORT DESCRIPTION OF THE DRAWING FIGURES

FIG. 1 is a perspective view of an elongated, disposable biohazard shielding bag, of transparent plastic material disposed along the inner surface of a trapezoidal sheet, or cover, of padded foldable material, the bag being closed on the vertical forward end, open on the after end and zippered shut along the top;

FIG. 2 is a top plan view;

FIG. 3 is a side elevation, to an enlarged scale, as viewed from the left-hand side of FIG. 2;

FIG. 10 is a fragmentary cross-sectional view, to an enlarged scale, showing the laminated structure of the sheet, the section being taken on the line 10—10 in FIG. 2;

FIG. 11 is an exploded perspective view of the bottom of a second form of the combination, termed a crossbar traction splint cover (CTSC), showing a splint of the Ischial Pad type preparatory to being inserted into the biohazard shielding bag;

FIG. 12 is a bottom plan view of the CTSC prior to insertion of the emergency traction splint into the biohazard shielding bag;

DETAILED DESCRIPTION OF PREFERRED FORMS OF THE INVENTION

Figure 4:
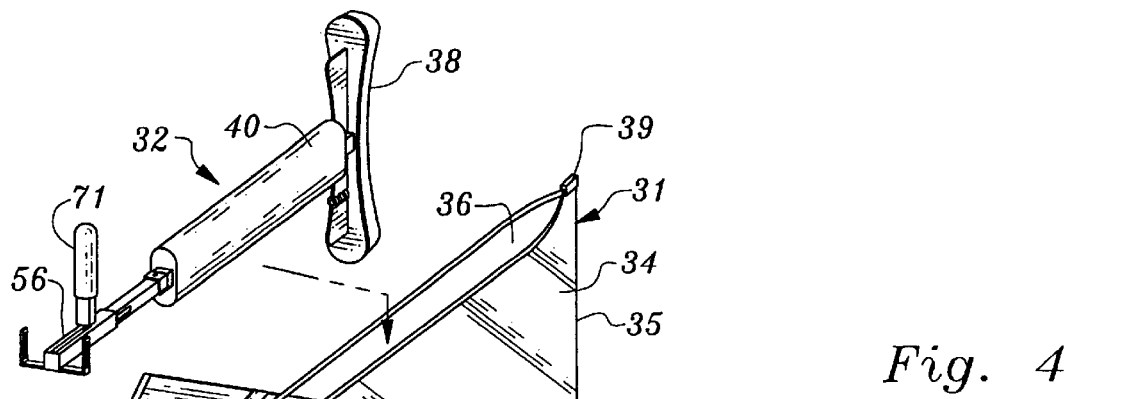
FIG. 4 is a view comparable to FIG. 1 but with the top of the bag unzipped, ready to receive the SAGER® Emergency Traction Splint shown.

Although the combined biohazard barrier and splinting device of the invention can be embodied in various forms, depending in large part upon the type of emergency traction splint utilized, two preferred forms, one for use with the SAGER® splint and one with the crossbar ischial pad type of traction splint are disclosed herein.

The combination of the invention, generally designated by the reference numeral 11, includes in both cases, a sheet 12, or cover, of pliable material (see FIG. 10).

Preferably, the sheet 12, or cover, is of a laminated construction in which a middle layer 13, is sandwiched between an upper layer (the patient surface) 14 made, for example, of DuPont's TYVEK® spunbonded olefin Type 1422 B, or other suitable soft, malleable cloth-like material, and a lower layer (the outside surface) 15 made of DuPont's TYVEK® Type 1073 A, or other suitable stronger and stiffer material.

The middle layer 13 can be of conventional bubble-pack construction or, preferably, comprises a plurality of individual elongated batts 16 separated by longitudinal grooves 17. In either case, the intermediate, padded layer 13 provides the major portion of the splinting ability of the cover 12. In other words, the cover portion of the present combination is usable as a good splint even without a traction splint.

The cover 12 extends longitudinally between a forward end 18 and an after end 19 and transversely between a first lateral edge 20 and a second lateral edge 21. The overall configuration of the cover 12 is generally trapezoidal in form, as can best be seen in FIG. 2, showing a top plan of a SAGER® Traction Splint Cover (STSC) and in FIG. 12, showing a bottom plan of a Crossbar Traction Splint Cover (CTSC).

On both embodiments, the elongated batts 16 can be of a matted fiber and are held in place by stitching 22 around the entire periphery of the trapezoidal covers 12 and by two spaced-apart rows of stitching 23 along the margins of each of the longitudinal grooves 17. (see FIG. 10).

Figure 5:
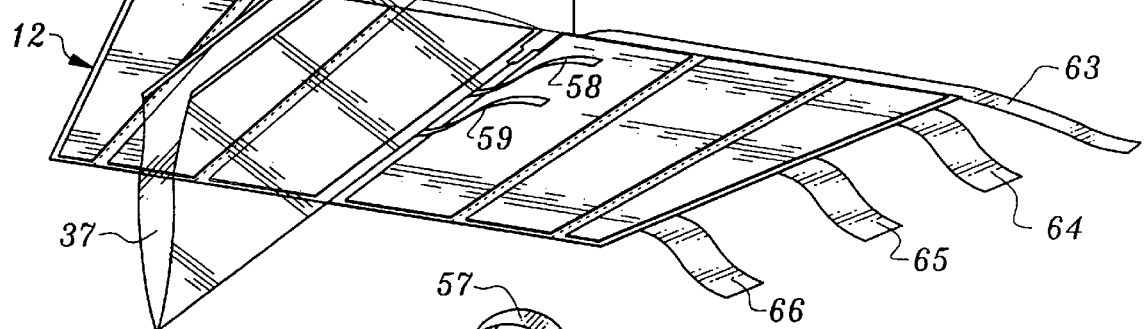
FIG. 5 is a view comparable to FIG. 4, but with the sides of the biohazard shielding bag folded into enclosing relation with respect to the SAGER splint.
Figure 6:
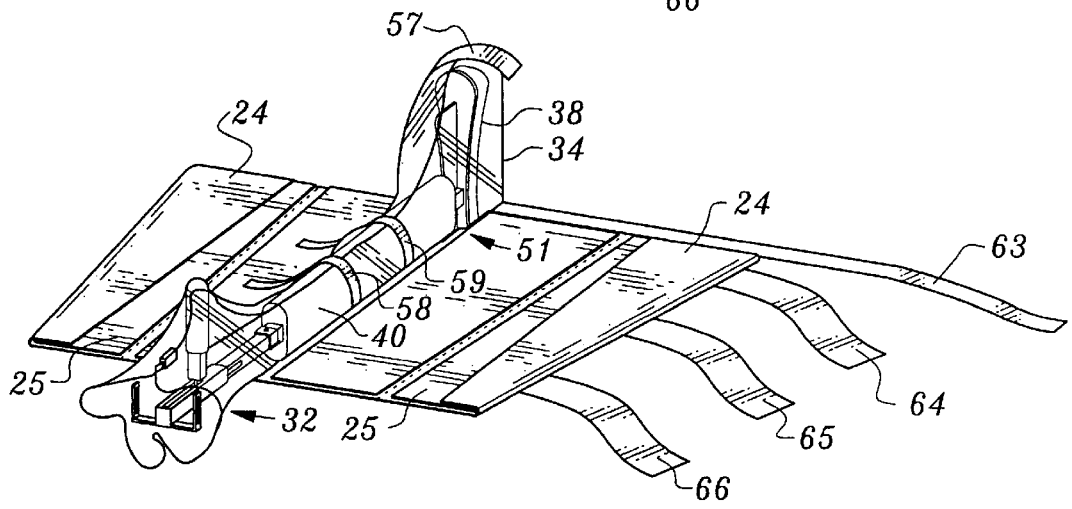
FIG. 6 is a view comparable to FIG. 5, but with the outermost wings of the trapezoidal sheet folded inwardly to reduce the size for fitting a small patient.

One of the several benefits resulting from the batt and groove construction described above arises from the hinge, or pivot, capability which allows the two outermost batts 24, or wings, to be folded over the respective adjacent batts 25, as shown in FIGS. 5 and 6. By folding over the batts 24 along the grooves between the respective batts 24 and batts 25, the size of the cover 12 is reduced to accommodate the requirements of a small adult or a child.

In addition to the disposable splint cover 12, the combination of the present invention also includes a disposable biohazard barrier 31, or shield, especially designed to cooperate both with the cover 12 and with a reusable emergency traction splint, such as a SAGER® splint 32 (see FIG. 4) or a crossbar ischial pad traction splint 33 (see FIG. 11).

The shape of the barrier 31 differs somewhat, depending upon which type of emergency traction splint is used. In any case, the barrier 31 is, in essence, an elongated container, or bag, capable of receiving the particular emergency traction splint to be used. Preferably, the bag is of transparent impervious flexible plastic material.

In the case of a SAGER® splint, the barrier 31 is an elongated bag 34 which has a height substantially exceeding the width (see FIG. 1). The bag 34 is closed at the front end 35, adjacent the forward end 18 of the cover 12, and can be zipped open along the uppermost portion 36 by fastener 39. The open rear end 37 is located in the general vicinity of the after end of the cover 12. The openings make it convenient to insert into the bag 34 a SAGER® splint 32, as shown in FIG. 4. The closed front end 35 is large enough to accommodate the ischial perineal cushion structure 38 of the splint 32 (see FIG. 5).

In the event that a crossbar ischial pad traction splint 33 is used, the barrier 31 includes an elongated bag 41 closed at the forward end 42 and open at the after end 43 to receive the crossbar splint 33. To facilitate insertion of the splint 33, into the bag 41, the entire bag is wide enough and of sufficient height and flexibility readily to receive the ischial pad 46 and the rectangular framework 47 of the splint 33 (see FIGS. 11, 13 and 14).

In order to provide optimum biohazard shielding, yet provide access to the traction mechanism for manipulation by the medical attendant at the accident site, strategically located bag securing means 51 are provided.

Thus, in the event a SAGER® splint 32 is used, as most clearly appears in FIGS. 4, 5 and 6, the transparent plastic bag 34, or container, is arranged so that the closed front end 35 of the bag extends somewhat beyond the forward end 18 of the cover 12. More particularly, the front end portion 53 of the bag 34 overlies a longitudinal slot 54, or opening, in the central forward end 18 of the cover (see FIG. 2). The opening 54 is large enough to accommodate the bottom portion of the ischial perineal cushion structure 38 of the SAGER® splint 32 when the splint is inserted in the flexible plastic bag 34 (see FIGS. 5 and 6).

With the splint 32 inserted in the bag 34, the top 36 zippered shut and the covered lower portion of the ischial perineal cushion extending downwardly through the opening 54, the rear end 37 of the bag 34 extends rearwardly from the foot or after portion, of the splint 32 far enough to cover generously all of the dynamic tensioning structure 56 of the splint 32.

After the bag 34 is snugly wrapped around the enclosed portion of the splint 32, a forward transverse flap 57 (see FIGS. 2, 5 and 6) mounted at one end on the bottom front end of the bag 34 is used to embrace the portion of the bag covering the ischial perineal cushion structure 38 of the splint 32. A spaced pair of transverse flaps 58 and 59, secured at one end to the bottom of the bag 34 and/or the adjacent portion of the cover 12, are also utilized to hold the bag firmly in closed position around the splint cushion 40, as shown in FIGS. 5 and 6.

Any suitable arrangement for causing the flaps to maintain a snug closed position can be used, including VELCRO or adhesive surfaces protected by peelable strips until ready for use.

In order to enhance the effectiveness of the biohazard shield previously described and to augment the splinting and alignment functions of the traction splint 32, the assembled components, as shown in FIG. 5 or FIG. 6, are placed under the injured leg or legs of the patient, depending upon whether the injury is unilateral or bilateral.

In either case, the relative position of the components and patient is adjusted so that the ischial perineal cushion is accurately lodged against the ischial tuberosity of the patient in the manner directed by the manufacturer's instructions. The cover 12 then is wrapped snugly about the injured leg(s) as well as the major portion of the traction splint 32 which is firmly covered and secured within the bag 34.

The cover 12, in other words, then becomes an enclosure 61 having a substantially medial axis more or less coincident with the patient's leg(s). The folded cover 12 is firmly secured to provide additional splinting by means of transverse strips (having VELCRO or adhesive surfaces protected by peelable covers until ready for use) including a thigh strap 63 and a plurality of strips 64, 65 and 66, all mounted at one end on the cover 12 (see FIGS. 4–6 and 8 and 9). The thigh strap 63 is adjusted to make sure it is snug and secure.

Figure 7:
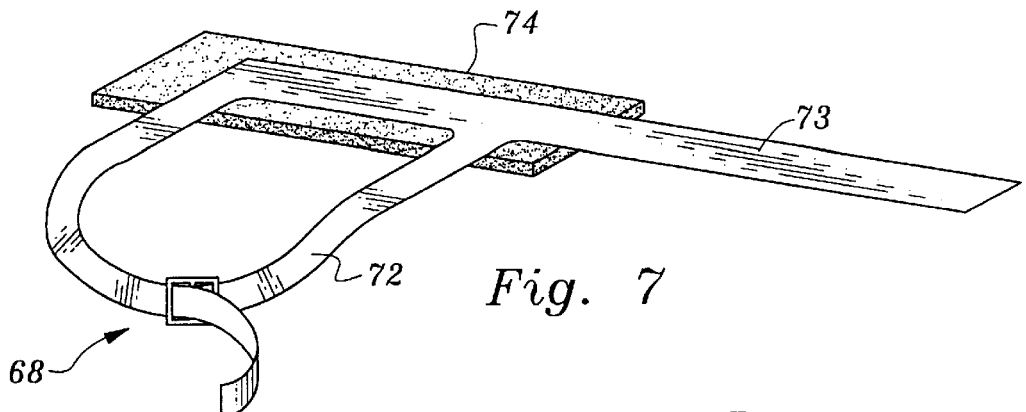
FIG. 7 is a perspective view of an ankle harness in developed position.
Figure 8:
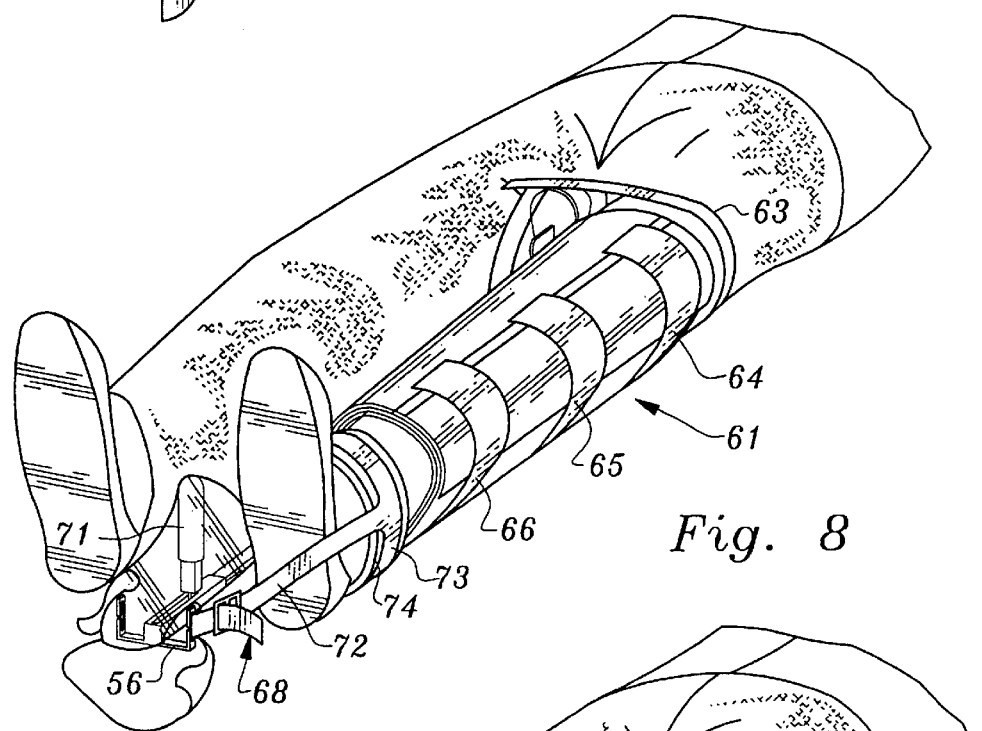
FIG. 8 is a perspective view of a preferred embodiment of the invention installed on a patient having a single, or unilateral, fracture.
Figure 9:
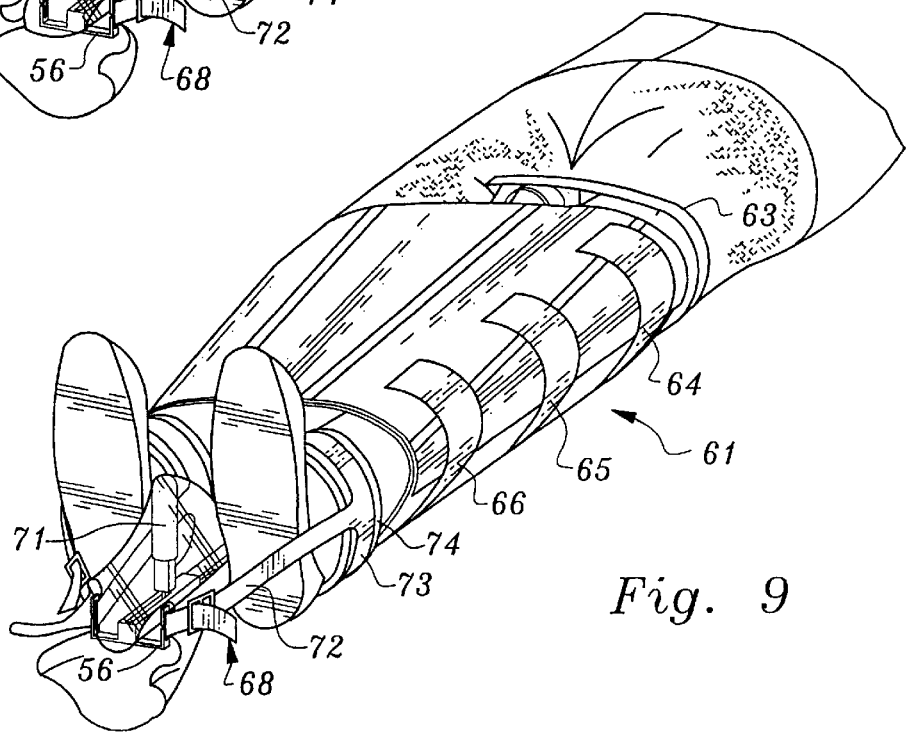
FIG. 9 is a perspective view of a preferred embodiment of the invention installed in a bilateral arrangement.

Dynamic tension is established in the traction splint 32 by the interaction of the splint tensioning structure 56 and a malleolar harness 68, or ankle harness, illustrated in developed position in FIG. 7 and in operative position in FIGS. 8 and 9. The ankle harness 68 applies traction to the leg as the medical attendant grasps both the bag-covered body of the splint 32 and the traction handle 71 of the splint 32 and carefully applies the recommended traction amount. Access to the handle 71 is obtained by reaching into the open rear end 37 of bag 34.

In other words, as the handle 71 is urged in a direction away from the ischial perineal cushion structure 38 while keeping the cushion 38 firmly lodged against the ischial tuberosity of the patient, the rearward movement of the traction handle 71 is transmitted through the buckled strap 72 to the ankle harness loop 73 and pad 74 snugly encircling the ankle (see FIGS. 8 and 9). Traction in the appropriate amount is thereby applied to the injured leg(s), the counterforce being applied to the ischial tuberosity which remains fixed and immobile. After traction is applied, the rear end portion of the flexible bag 34 can be folded shut if desired and pushed forwardly into any available tight crease in the ankle harness structure.

The biohazard barrier and splinting device when used in conjunction with the Ischial Pad type of splint 33 functions in a manner quite similar to that recited above in connection with the SAGER® splint 32, as will now be described.

The biohazard barrier bag 41 is shaped to conform to the configuration of the crossbar splint 33 (see FIG. 11) and is therefore laterally widened to provide ready insertion of the ischial pad 46 and the rectangular framework 47, as previously pointed out.

Figure 13:
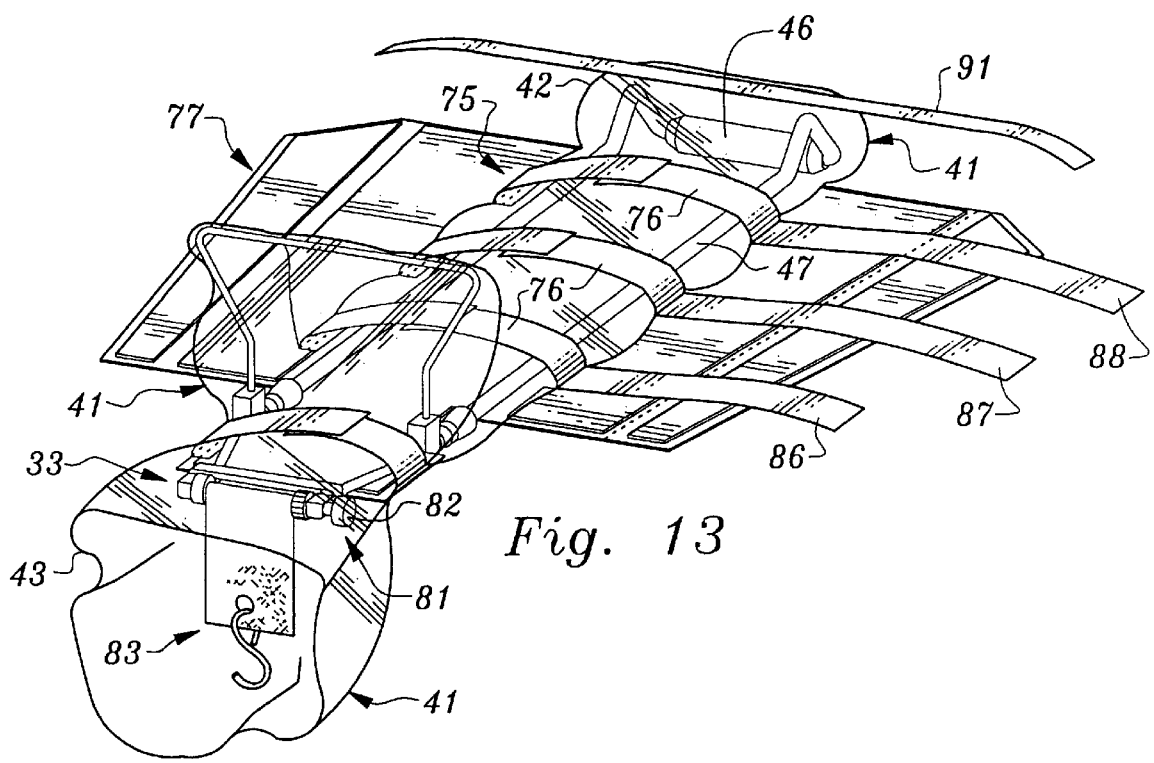
FIG. 13 is a perspective view of the underneath, or bottomside, of the CTSC, with the emergency traction splint inserted into the bag and strapped in shielded mode, preparatory to being turned over and inserted under a patient.

The bag 41, when wrapped tightly around the crossbar splint 33 as in FIG. 13, is secured by fastening means 75 including a plurality of transverse elongated flaps 76 each spaced apart longitudinally and having one end made fast to the flexible cover 77, or sheet.

The ischial pad 46 of the crossbar splint 33 is located in the front end of the bag 41 and the traction inducing component 81, (including the ratchet traction handle 82 and the "S" ring hook 83, as well as the heel stand 84) is located forwardly from the after end of the bag 41.

Figure 14:
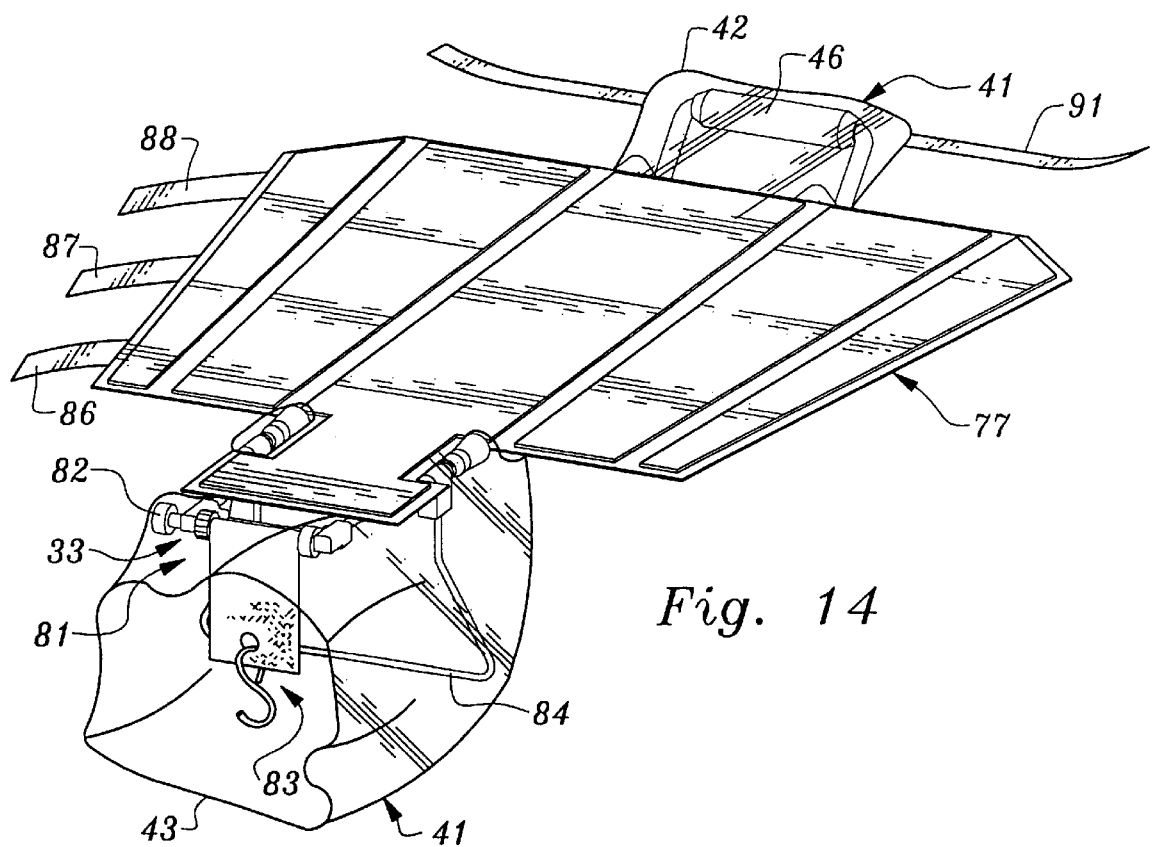
FIG. 14 is a perspective view of the upper, or patient side of a readied CTSC.
Figure 15:
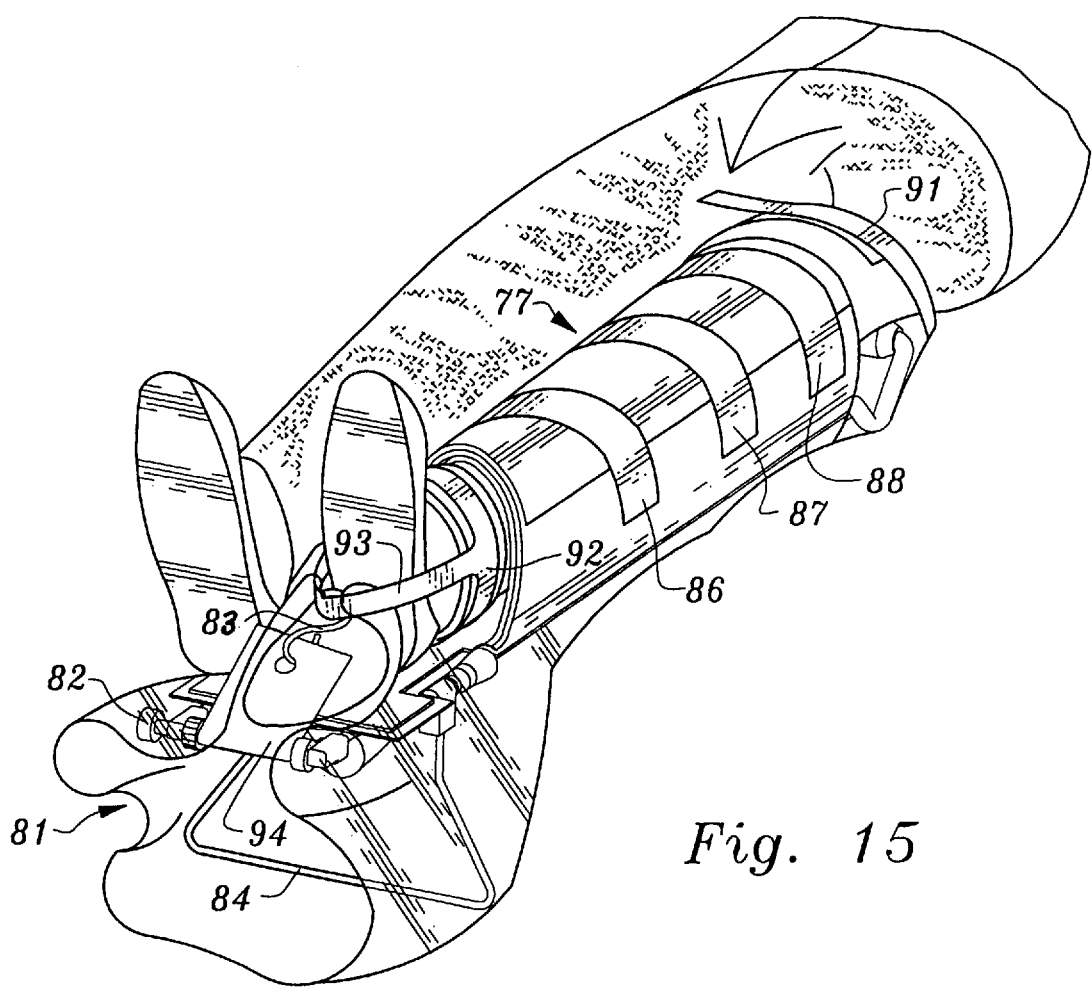
FIG. 15 is a perspective view of a biohazard shielding combination with a CTSC form of splint installed in traction mode on the injured left leg of a patient and with the after end of the flexible bag preparatory to being folded and tucked into enclosing relation with respect to the Ischial Pad splint.

The crossbar traction splint cover (CTSC) 77 includes flexible strips 86, 87 and 88 (provided either with VELCRO or with adhesive surfaces protected by peelable covers until ready for use) for securing the cover 77 after the device is inverted from the position shown in FIG. 13 to that shown in FIG. 14 and is folded around the injured leg, as illustrated in FIG. 15, to form a snug cylindrical protective enclosure.

A thigh strap 91 is used, as before, to secure the device firmly in the thigh area of the patient and an ankle harness 92 includes a strap 93 engageable with the "S" ring hook 83 so that as tension is applied by rotation of the ratchet traction handle 82, the traction imposed on the ankle harness 92 via the web belt 94, the "S" ring hook 83 and the strap 93 is transmitted to the injured leg and applies the appropriate traction to the leg. The extra long after end 43 of the flexible bag 41 is then folded shut and pushed forwardly where it is tucked into any available tight crease, as described above in connection with the SAGER splint.

After the patient is transported to the hospital or other medical facility and the necessary steps are taken, including removal of the ankle harness, the plastic bag shielding the emergency traction splint and the cylindrical enclosure, or cover, all of the components except the emergency traction splint are disposed of.

What is claimed is:

1. A combined biohazard barrier and splinting device comprising:
    a. a sheet of pliable material having an outer surface and an inner surface, said sheet extending longitudinally between an upper end and a lower end and transversely between a first lateral edge and a second lateral edge, said sheet being foldable about a longitudinal substantially medial axis to form an enclosure capable of surrounding an injured leg of a human being with said inner surface facing toward the injured leg;
    b. an elongated bag of pliable material disposed on said inner surface of said sheet and extending between a first end adjacent said upper end of said sheet and a second end terminating in the vicinity of said lower end of said sheet, said bag having a size capable of receiving an emergency traction splint;
    c. fastening means for securing said bag in biohazard shielding mode around the splint; and,
    d. means for holding said enclosure in snug relation around the injured leg, the splint and said bag in biohazard shielding mode.

2. A combination as in claim 1 in which said sheet is substantially trapezoidal in plan in developed condition.

3. A combination as in claim 1 in which the splint is an emergency traction splint of the type including an ischial perineal cushion and a traction handle portion and said elongated bag is closed at said first end, open at said second end and is sufficiently wide at said first end to accommodate the ischial perineal cushion of the splint.

4. A combination as in claim 3 in which the length of said elongated bag is such that the traction handle portion of the splint can be reached when the splint is in biohazard shielding mode in said bag, the ischial perineal cushion is ready to be lodged against the ischial tuberosity of the patient having the injured leg and traction is applied.

5. A combination as in claim 4 in which said bag securing means includes a plurality of flexible transverse elongated flaps, each spaced apart longitudinally and having one end fastened to said sheet.

6. A combination as in claim 5 in which said enclosure holding means includes a plurality of strips of flexible material mounted at one end on said sheet and being capable of being folded over and fastened to said outer surface of said sheet folded into enclosure form.

7. A combination as in claims 5 and 6 in which said flaps and said strips include surface layers of adhesive protected by peelable covers until ready to be used.

8. A combination as in claim 1 in which the splint is of the crossbar ischial pad traction type and said elongated bag is closed at said first end and open at said second end, said bag being of sufficient transverse width to receive the ischial pad and the frame of the splint; and being of sufficient length to enclose the traction inducing components of the splint but allowing the components to be reached when traction is applied.

9. A combination as in claim 8 in which said bag securing means and said enclosure holding means comprise a plurality of flexible bands mounted at one end on said sheet and being capable of adhering to the surface of other bands in contact therewith.

10. A combination as in claim 1 in which said sheet is of laminated construction including a layer of soft, malleable spunbonded olefin and a stronger and stiffer layer of spunbonded olefin.

11. A combination as in claim 10 including an intermediate layer of padding material.

\* \* \* \* \*